US005578043A

United States Patent [19]
Galstian

[11] Patent Number: 5,578,043
[45] Date of Patent: Nov. 26, 1996

[54] DELIVERY HELMET FOR LOW BIRTH WEIGHT INFANTS

[76] Inventor: Arthur Galstian, 201 Pennsylvania Pkwy., Suite 300, Indianapolis, India. 46280

[21] Appl. No.: 321,177

[22] Filed: Oct. 11, 1994

[51] Int. Cl.$^6$ ............................ A61B 17/41; A61B 17/02
[52] U.S. Cl. ............................................ 606/119; 606/122
[58] Field of Search ..................................... 606/122, 123, 606/124, 119, 121; 128/20

[56] References Cited

U.S. PATENT DOCUMENTS

| | | | |
|---|---|---|---|
| 2,219,424 | 10/1940 | Breck | 606/122 |
| 2,637,320 | 5/1953 | Greenburg | 606/122 |
| 3,665,925 | 5/1972 | Dersookian . | |
| 3,785,381 | 1/1974 | Lower et al. . | |
| 3,789,849 | 2/1974 | Laufe | 606/122 |
| 4,151,846 | 5/1979 | Von Zeppelin et al. . | |
| 5,139,503 | 8/1992 | Salas-Ceniceros | 606/122 |

OTHER PUBLICATIONS

David C. Shaver, M.D. et al., "Early and Late Intraventricular Hemorrhage: The Role of Obstetric Factors," *Obstetrics & Gynecology*, vol. 80, No. 5, Nov. 1992 pp. 831–837.

Mark C. Williams, M.D. et al., "Obstetric Correlates of Neonatal Retinal Hemorrhage", *Obstetrics & Gynecology*, vol. 81, No. 5, Part 1, May 1993, pp. 688–694.

Mortimer G. Rosen, M.D. et al., "Abnormal Labor and Infant Brain Damage," *Obstetrics & Gynecology*, vol. 80, No. 6, Dec. 1992 pp. 961–965.

Michael H. Malloy et al., "Increasing Cesarean Section Rates in Very Low–Birth Weight Infants: Effect on Outcome." *Operative Obstetrics and Anesthesia, J. Am. Med. Assoc.* 262:1475, 1989, pp. 185–187.

The Victorian Infant Collaborative Study Gorup, "Improvement of Outcome For Infants of Birth Weight Under 1000g," *Obstetrical and Gynecological Survey*, Arch. Dis. Child. 66:765, 1991 pp. 108–110.

Joseph J. Volpe, MD, "Intraventricular Hemorrhage and Brain Injury in the Premature Infant—Diagnosis, Prognosis, and Prevention," *Clinics in Perinatology*, vol. 16, No. 2, Jun. 1989, pp. 387–411.

Joseph J. Volpe, M.D., "Intraventricular Hemorrhage and Brain Injury in the Premature Infant—Neuropathology and Pathogenesis," *Clinics in Perinatology*, vol. 16, No. 2, Jun. 1989, pp. 361–385.

*Primary Examiner*—Michael A. Brown
*Attorney, Agent, or Firm*—Woodard, Emhardt, Naughton, Moriarty & McNett

[57] ABSTRACT

The present invention provides a delivery helmet for sensing and indicating the longitudinal movement of a fetal head within the maternal birth canal. The delivery helmet is designed to protect a low birth weight fetal head during delivery and thereby minimize the the traumatic intracranial hemorrhaging that may result during spontaneous birth. A pair of members are constructed for insertion into operative association between the fetal head and the mother. Each member includes a portion for contacting and partially surrounding the fetal head. A movement indicator having an external display is mounted to the delivery helmet for detecting the longitudinal movement of the fetal head relative to the apparatus. As the fetus moves longitudinally relative to the delivery helmet, a signal is generated which provides an indication to the physician pertaining to the movement.

29 Claims, 6 Drawing Sheets

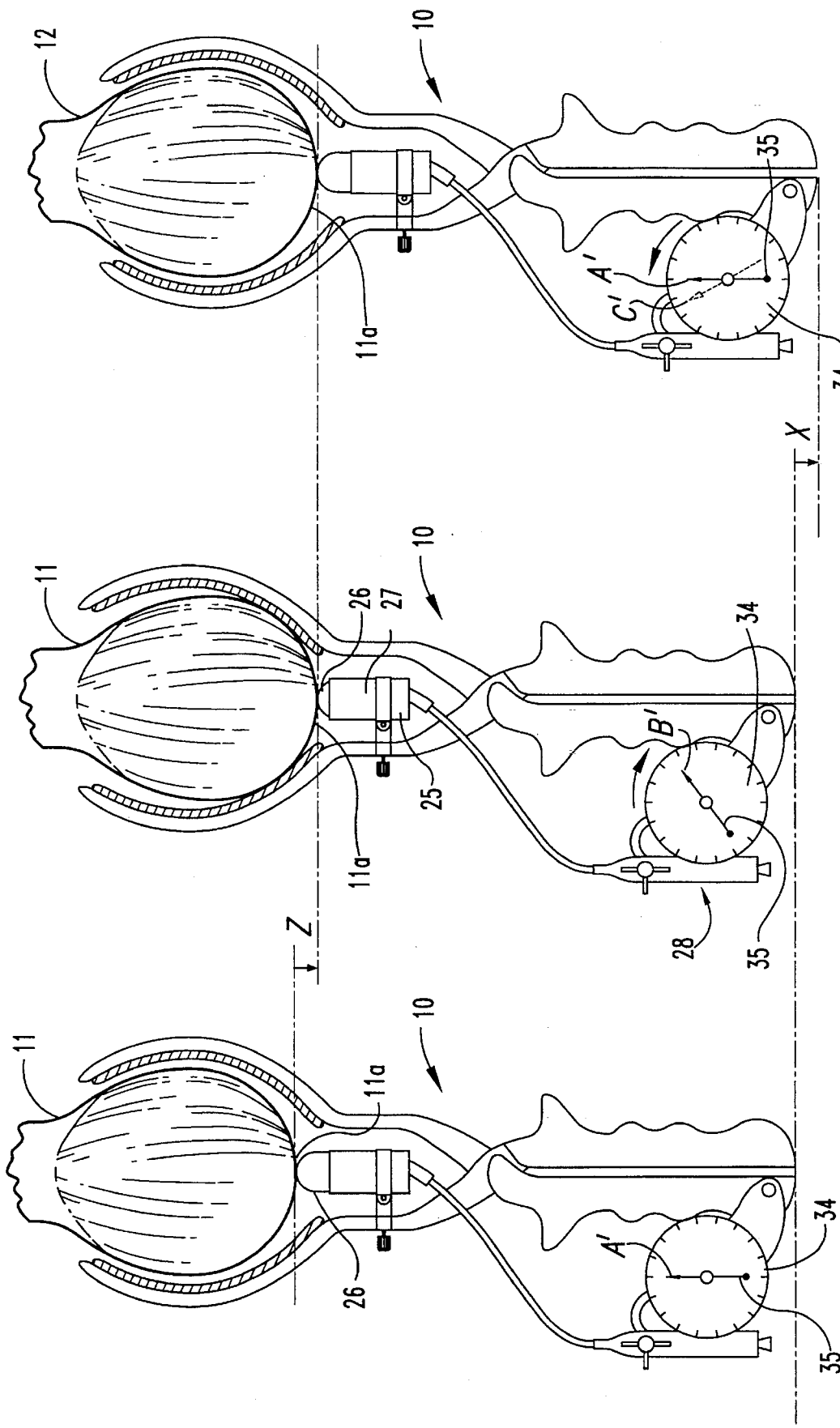

DELIVERY HELMET FOR LOW BIRTH WEIGHT INFANTS

BACKGROUND OF THE INVENTION

The present invention relates in general to obstetrical forceps for use in assisting in the delivery of a baby. More particularly, the present invention relates to a delivery helmet apparatus for sensing and indicating the longitudinal movement of the fetal head within the maternal birth canal.

The medical profession has been concerned with the morbidity and mortality of low birth weight infants. Since low birth weight fetuses are extremely vulnerable, two different approaches have been utilized in an attempt to minimize the traumatic consequences of spontaneous delivery. One approach has been the liberal usage of a Cesarean section. However, the use of Cesarean section delivery does not completely avoid trauma to low birth weight infants and additionally increases the rate of respiratory distress syndrome (RDS). Further, in an attempt to minimize trauma to the infant, the widening of the incision and inclusion of vertical incisions has been shown to increase the long term morbidity of the mother.

A second approach to minimize the traumatic consequences of a spontaneous delivery is to use an obstetrical forceps to assist with the delivery of the infant. Most of the obstetrical forceps are of the crossed or scissor type having cross branches or shafts with a pivot point located at an intermediate point along the shaft. The crossed forceps act as a lever and by virtue of the nature of the lever any compressive force applied to the handles is transmitted to the fetal engaging portion of the forceps and to the fetal head itself. Many infants delivered with the aid of obstetrical forceps have been clearly externally injured and possibly internally injured, although it has not been actually determined whether, and to what extent, internal injury has been caused.

Numerous obstetrical forceps have been designed and manufactured to assist in the delivery of the infant from the maternal birth canal. The previous forceps have generally been designed to substitute for maternal pushing efforts. In U.S. Pat. No. 3,665,925 to Dersookian there is described a forceps having a tension meter for indicating the amount of compressive force and tension applied to the fetal head during delivery. The Dersookian apparatus has a scale that enables the physician to observe the amount of pulling force being applied to the fetal head.

In U.S. Pat. No. 5,139,503 to Salas-Ceniceros there are disclosed obstetrical spatulas having a force indicator for displaying the force exerted on the spatulas. A handle is used to manipulate the spatulas during childbirth and the force indicator communicates the force exerted by the spatulas on the fetal head to enable the physician to adjust the pulling force applied in order to reduce or eliminate the possibility of injury.

In U.S. Pat. No. 3,785,381 to Lower and U.S. Pat. No. 3,789,849 to Laufe, there are disclosed forceps which are generally concerned with the sideways pressure applied to a fetal head. The Lower forceps include a pair of pivotally connectable blades having a pressure sensing device constructed on one of the forceps' blades. The sideways pressure exerted on the fetal head by the forceps is sensed by the sensing device and displayed on a gauge that is observable to the attending physician. When the sideways pressure received by the fetal head reaches a predetermined magnitude, the physician can reduce his hand grip on the forceps in order to correspondingly reduce the sideways pressure on the fetal head.

In Laufe there is described an obstetrical forceps that signals or indicates to the physician that a predetermined compressive force has been exceeded, and that it may be desirable to reduce the force asserted on the forceps to avoid injuring the fetal head. The Laufe forceps incorporates a shiftable blade that changes position when an external force applied to the forceps exceeds a predetermined value. An internal spring within the forceps is utilized to maintain the handle in its normal non-slipped position. However, when the compressive and traction forces exceed the spring force the handle shifts, thereby signaling the physician to reduce his hand grip and the corresponding force being applied.

Even with the variety of earlier designs of obstetrical forceps there remains a need for an improved obstetrical forceps. A need remains for an obstetrical forceps that coordinates withdrawing the forceps to correspond with the natural longitudinal movement of the fetus through the maternal birth canal. The present invention satisfies this need in a novel and unobvious way.

SUMMARY OF THE INVENTION

To address the unmet needs of prior obstetrical forceps, one form of the present invention contemplates an apparatus in the preferred embodiment for assisting in the delivery of a low birth weight baby comprising a pair of first members for insertion into operative association with a fetal head, each of the first members having a first end defining a fetal head engaging portion and an opposite second end; a second member connecting the pair of first members; and, a movement indicator mounted to the apparatus for detecting and communicating the longitudinal movement of the fetal head relative to the apparatus.

A second form of the present invention is an apparatus for assisting in the delivery of a baby comprising: a delivery helmet disposed between a fetal head and a maternal birth canal for protecting the fetal head; and, a position indicator mounted to the delivery helmet, the position indicator sensing and communicating the longitudinal movement of the fetal head relative to the helmet.

One object of one form of the present invention is to provide head protection for assisting in the delivery of a low birth weight baby.

Related objects and advantages of the present invention will be apparent from the following description.

BRIEF DESCRIPTION OF THE DRAWINGS

FIG. 5a is a full sectional view of the delivery helmet of FIG. 4 taken along line 5a–5a.

FIG. 6a is an illustrative view of the delivery helmet of FIG. 1 in its initial position.

FIG. 6b is an illustrative view of the delivery helmet of FIG. 1 after the infant has moved longitudinally in the maternal birth canal.

FIG. 6c is an illustrative view of the delivery helmet of FIG. 1 after the attending physician has withdrawn the delivery helmet to its initial position relative to the fetal head.

DESCRIPTION OF THE PREFERRED EMBODIMENT

Figure 1:
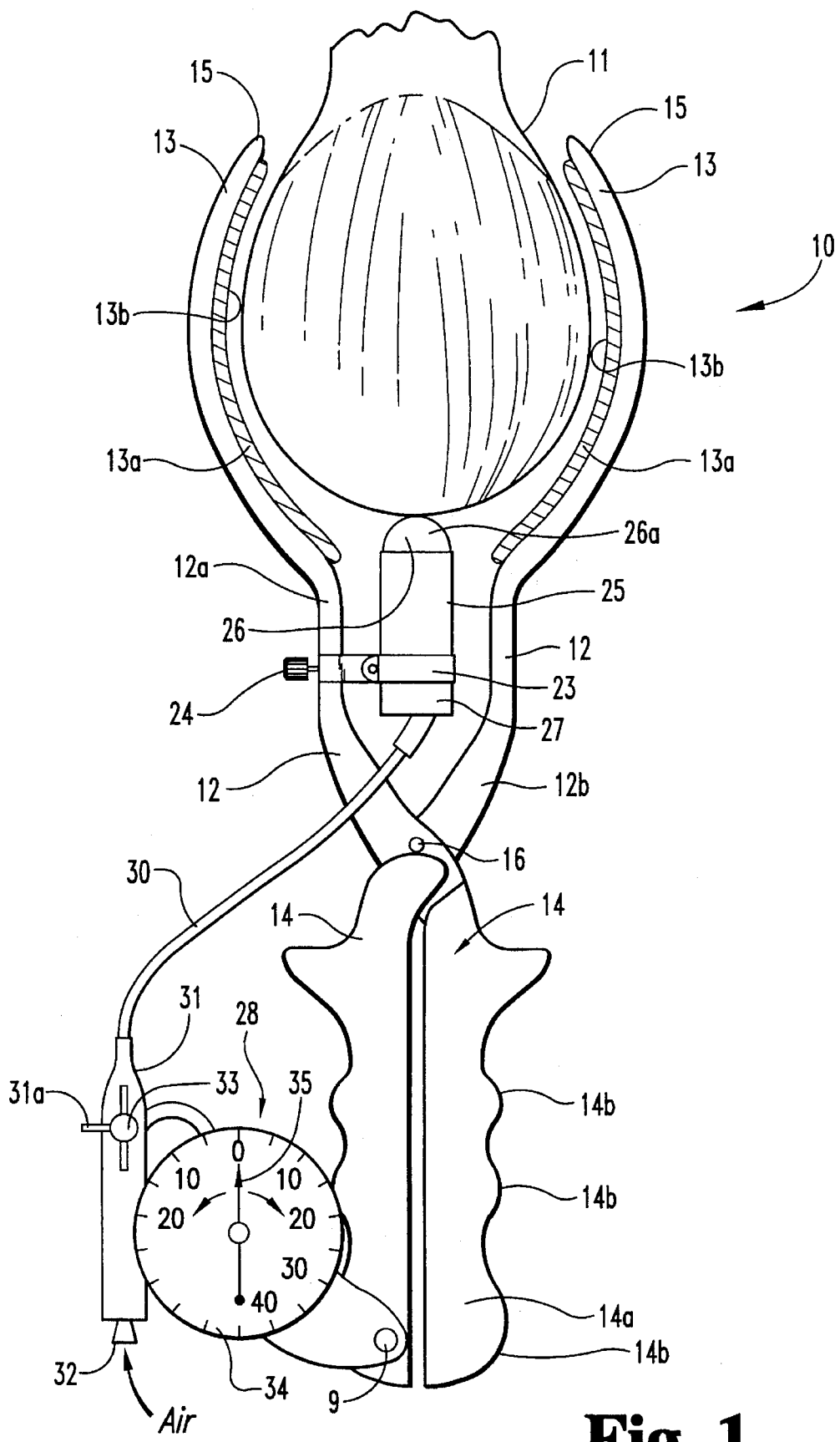
FIG. 1 is a top plan view of a delivery helmet according to one embodiment of the present invention positioned adjacent a fetal head.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is illustrated a delivery helmet 10 which is designed and manufactured in accordance with the present invention. Delivery helmet 10 is designed to provide protection for a premature fetal head 11 during delivery to minimize traumatic intracranial hemorrhaging that may result during spontaneous preterm birth. The delivery helmet 10 is designed to protect the fragile fetal head from the traumatizing action of the rigid birth canal and perineal tissue, and not to replace the maternal forces for fetal delivery through the birth canal. The delivery helmet 10 of he preferred embodiment includes a pair of first members 12 having a fetal head engaging portion 13, and an opposite handle portion 14 that is suitable for grasping by an attending physician. In the preferred embodiment the first members 12 are formed from a material inert to bodily fluids, such as stainless steel or titanium.

The pair of first members 12 are joined together with a second member 16. In the preferred embodiment, the second member 16 defines a hinge pin that is affixed to one of the first members 12, and the other first member 12 has a corresponding bore formed therein for receiving the second member 16. With this design of the preferred embodiment the pair of first members 12 can be readily assembled and disassembled by the positioning of the hinge pin 16 within the bore formed in the opposite first member 12. The ease of assembly and disassembly facilitates storage, cleaning, and the manipulation of the delivery helmet 10.

Delivery helmet 10 is comprised of a pair of first members 12 that can be viewed or thought of as having two sections or portions. The handle portion 14 is disposed on the proximal end 14a of each of the first members 12 to facilitate the physicians manipulation of delivery helmet 10. The handle position 14 includes a series of protuberances 14b designed to interengage with the physician's fingers. In the preferred embodiment the protuberances 14b are integrally formed on the handle portion 14. However, an alternate embodiment contemplates an elastomeric covering having protuberances positioned over the handle portion 14.

The fetal head engaging portions 13 are integrally formed on a first end 15 of each of first members 12 for utilization in operative association with the fetal head during delivery. The fetal head engaging portion 13 defines a cup-shaped blade for protecting the fetal head from trauma, and is not designed for grasping or pulling on the fetal head. In the preferred embodiment the fetal head engaging portion 13 has a liner 13a attached thereto. The liner 13a is preferably a soft elastomeric material defining a surface 13b for the fetal head 11 to contact, thereby minimizing or decreasing any concentrated point loading and acting as a bumper for the fetal head 11.

First member 12a of the pair of first members 12 has a movement indicator 23 attached thereto. In the preferred embodiment the movement indicator 23 is attached to the first member 12a by a set screw 24. Movement indicator 23 is initially positioned adjacent the crown 11a of the fetal head 11. The movement indicator 23 includes a sensor 25 having a plunger 26 that is placed in contact with the fetal head 11. The plunger 26 is slideably disposed within a tube 27 of sensor 25. The plunger 26 moves axially in the tube 27 corresponding to the longitudinal movement of the fetal head 11 through the maternal birth canal during delivery. In the preferred embodiment the plunger 26 has a spherical shaped end 26a. The spherical shaped end 26a is manufactured from an elastomeric material in order to minimize trauma or injury to the fetal head 11. The movement indicator 23 functions to detect and communicate to the attending physician the longitudinal movement of the fetal head 11 relative to the delivery helmet 10.

Movement indicator 23 is connected to a manometer 28 that is affixed to the handle portion 14 of first member 12b. The manometer 28 is connected to the handle portion 14 by a fastener 9. The fastener is externally threaded and is received within a correspondingly internally threaded bore formed in the handle portion 14. Other fasteners contemplated include rivets, adhesive, and a nut and bolt combination.

A conduit 30 provides a pathway for fluid flow between the movement indicator 23 and the manometer 28. The conduit 30 is formed from a flexible material that can be easily re-shaped. In the preferred embodiment, the fluid utilized in the movement indicator 23 and manometer 28 is drawn from the ambient air surrounding the delivery helmet 10. Ambient air generally comprises a mixture of invisible, odorless, tasteless gases such as nitrogen and oxygen.

Manometer 28 includes a connecting body 31 having a fluid inlet location 32 for allowing the introduction of fluid into conduit 30, movement indicator 23, and manometer 28. A control valve 33 is disposed within the connecting body 31 and a handle 31a is moveable to control the fluid flow within the apparatus. In one position the valve 33 allows the fluid to fill the movement indicator 23, manometer 28, and conduit 30; and in a second position the valve 33 allows fluid flow between movement indicator 23 and manometer 28 without exposure to the atmosphere. In the preferred embodiment a dial indicator 34 displays changes in pressure to the physician which correspond to the longitudinal movement of fetal head 11 relative to delivery helmet 10.

Figure 2:
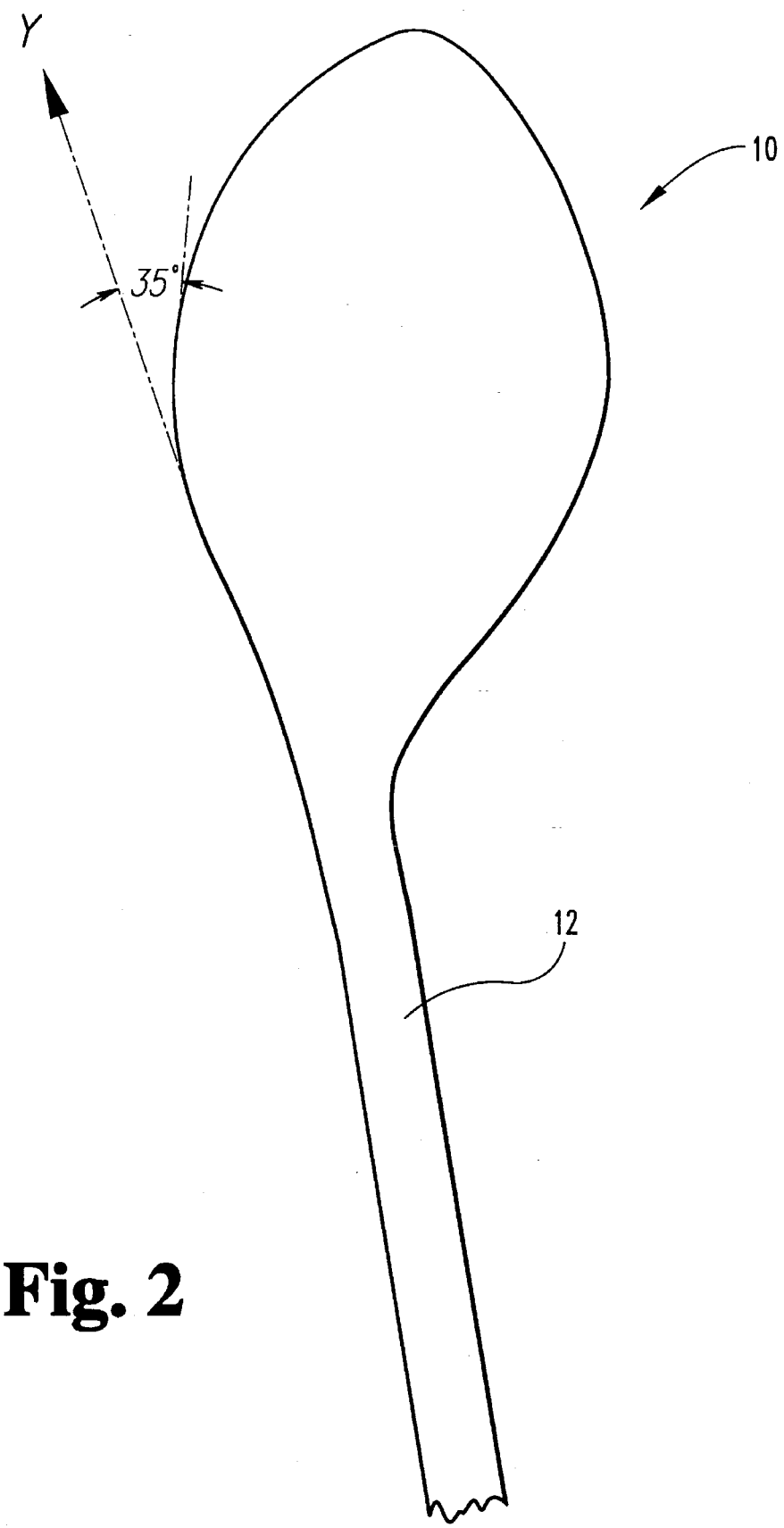
FIG. 2 is a side elevational view of the delivery helmet of FIG. 1.
Figure 3:
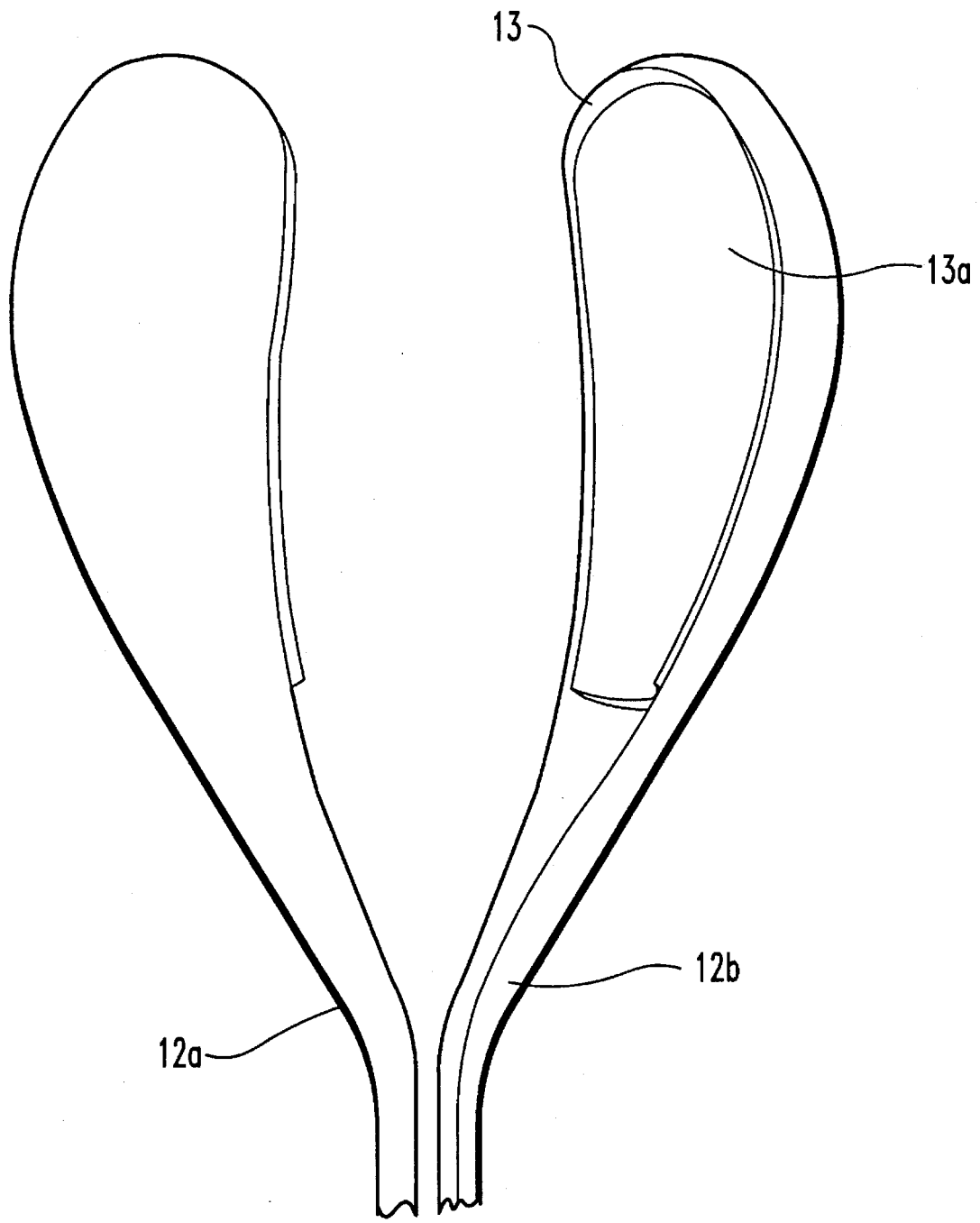
FIG. 3 is an isometric view of the delivery helmet of FIG. 1.

Referring to FIG. 2, there is illustrated a side elevational view of delivery helmet 10. The first member 12 is formed with a cephalic curve configuration such that the fetal head engaging portion 13 is formed at an angle of approximately 35° with a longitudinal axis Y to provide a perineal curve for the delivery helmet 10. With further reference to FIG. 3, there is illustrated the pair of first members 12 including the cupped fetal head engaging portions 13 having liners 13a for protecting the fetal head during the movement through the maternal birth canal. When the delivery helmet 10 is in a fully closed position the fetal head engagement portions 13 remain in a spaced apart relationship thereby minimizing the tendency to utilize delivery helmet 10 to pull or grasp the fetal head during delivery.

A compressive force is imparted by the fetal head 11 to the movement indicator 24 as the fetal head 11 moves longitudinally through the maternal birth canal. The fetal head 11 pushes the plunger 26 into the tube 27, thereby causing at least a portion of the fluid within the sensor 25 to be forced into the conduit 30 with a resulting impact on manometer 28. The associated movement of the plunger 26 increases the pressure of the fluid within the system which is indicated by a deflection of needle 35 of dial indicator 34. During the delivery of an infant a physician coordinates withdrawal of the delivery helmet 10 from the maternal birth canal in order to return the needle 35 substantially to the reference point "0". This coordination of movement returns the delivery helmet 10 to the initial position relative to the infant head 11 as shown in FIG. 1. The delivery time for an infant is not shortened by using a delivery helmet as usually is observed in forceps applications. Rather, the time and pace of delivery completely depends on natural maternal forces unless the fetus is placed in distress.

Figure 4:
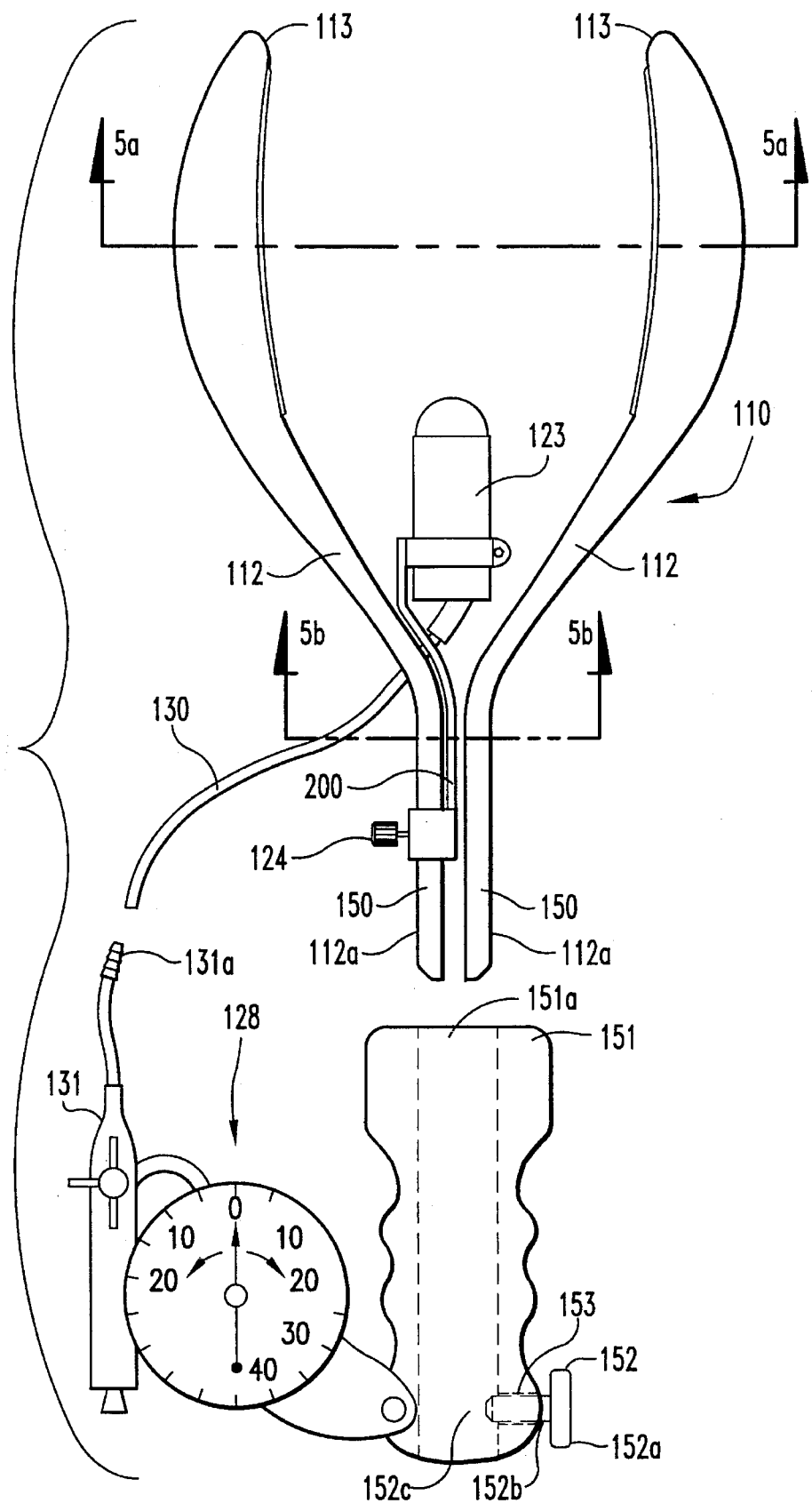
FIG. 4 is a partially exploded view of a delivery helmet according to another embodiment of the present invention.

The delivery helmet 110 illustrated in FIG. 4, corresponds to a second form of the present invention. The general construction and function of the corresponding delivery helmet 110 is virtually the same as delivery helmet 10 in many aspects. It should be noted that a 100 number prefix has been used for the reference numbers of FIGS. 1–3, for the like or similar structural features in drawings 4 and 5. In delivery helmet 110 the first members 112 include a fetal head engaging portion 113 and a shaft portion 150. The shaft portion 150 extends from the fetal head engaging portion 113. Shaft, portions 150 of first member 112 are removeably and slideably disposed within a detachable handle 151.

Handle 151 has a bore 151a formed longitudinally therethrough. The handle 151 is slidable along the pair of shaft portions 150 of first members 112. This allows handle 151 to be positioned at any location along the shaft portions 150 relative to the fetal head engaging portion 113 of first members 112 to improve the physicians ability to manipulate delivery helmet 110 and for easy adaptation of the movement indicator 123 adjacent the crown of the fetal head (not illustrated).

The movement indicator 123 is coaxially attached to one of the shaft portions 150 of first member 112. A mounting bracket 200 is coupled to the movement indicator 123 and attachable to the first member 112 by a set screw 124. A conduit 130 is formed from a flexible material and is designed for easy coupling with the connecting body 131 of manometer 128. The connecting body 131 includes a friction fitting 131a having a series of frustoconical rings for the conduit 130 to be attached on.

A thumbwheel 152 is connectable with the shaft portions 150 of first members 112 to lock the handle in a particular location. The locking thumbwheel 152 comprises an external hand engagement portion 152a, and an externally threaded fastener portion 152b. A bore 153 formed in handle 151 is internally threaded to correspond with the external threads of the fastener portion 152b. When the user tightens thumbwheel 152, it correspondingly draws an end 152c into contact with an outer surface 112a of at least one of the first members 112. The thumbwheel 152 functions to lock handle 151 in place on shaft portions 150.

Figure 5A:
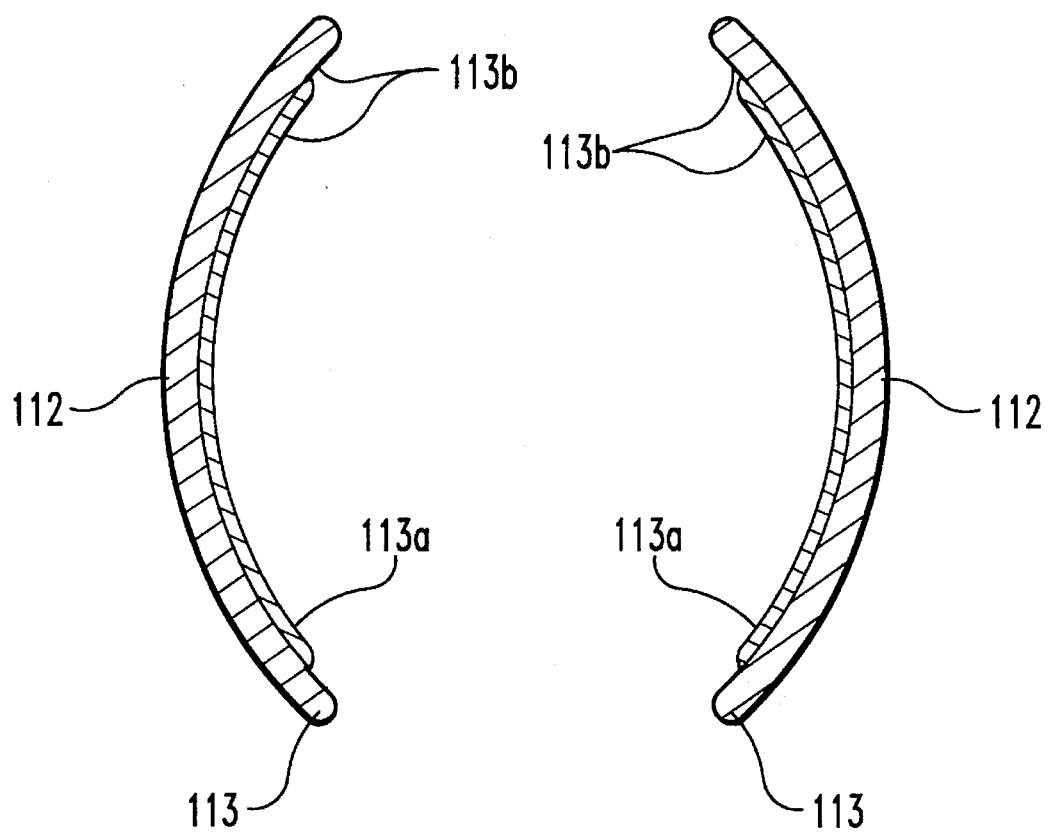
Figure 5B:
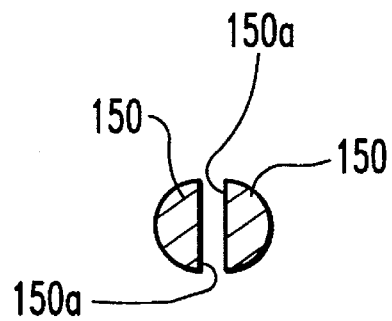
FIG. 5b is a full sectional view of the delivery helmet of FIG. 4 taken along line 5b–5b.

With reference to FIGS. 5a and 5b, there is illustrated a cross-sectional view of the fetal head engaging portion 113 and the shaft portion 150 of delivery helmet 110. The fetal head engaging portion 113 defines a cup-shaped blade which is designed for protecting the fetal head. Further, liner 113a defines a protective surface 113b for decreasing or minimizing the concentrated point loading on fetal head 11. The liner 113a is preferably constructed of a pliable elastomeric material which is inert to bodily fluids and can withstand frequent sterilizations. An alternate embodiment contemplates liners 113a which are removably attached to the delivery helmet 110, and are disposable.

In FIG. 5b, there is illustrated a cross-sectional view of the shaft portions 150 of first members 112. The cross-section of shaft portion 150 is D-shaped, with the flat surface 150a of each first member 112 being oriented to be contactable with the other.

With reference to FIGS. 6a–6c, an example is provided which illustrates how the delivery helmet 10 of the present invention is used to assist in the delivery of an infant. It is understood that this example would apply to delivery helmet 110 and any other embodiments of the present invention. This example, demonstrates the interaction between the delivery helmet 10, the fetal head 11, and the physician's associated response to signals from the delivery helmet 10 to aid in minimizing trauma to the infant. In FIG. 6a, there is illustrated the delivery helmet 10 positioned relative to the fetal head 11 in an initial position with plunger 26 contacting the crown 11a of the fetal head 11. At this relative position, the needle 35 of the dial indicator 34 is at a nominal reference position A'. With reference to FIG. 6b, there is illustrated the fetal head 11 after moving a distance Z longitudinally down the maternal birth canal. The movement of the fetal head 11 has pushed the plunger 26 within the tube 27 of the sensor 25, thereby exerting a force on the fluid in the system and causing the manometer 28 to indicate a change in state. As shown in FIG. 6b, the needle 35 of dial indicator 34 has been deflected to a new position B.

With reference to FIG. 6c, there is illustrated delivery helmet 10 after the physician has moved it outwardly a distance X relative to the mother's body. The physician continues to move the delivery helmet 10 outwardly until the needle 35 of the dial indicator 34 has returned to the initial reference position A'. When the needle 35 has been returned to the reference position A' the delivery helmet 10 has been moved sufficiently for the delivery helmet 10 to be positioned relative the fetal head 11 as it was in FIG. 6a. If a physician inadvertently withdraws the delivery helmet 10 further than required the dial indicator 34 displays a value, such as indicated by dotted line C' in FIG. 6c.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for assisting in the delivery of a baby, comprising:

a pair of first members for insertion into operative association with a fetal head, each said first member having a first end defining a fetal head engaging portion and an opposite second end;

a second member connecting said pair of first members; and a movement indicator mounted to the apparatus for detecting and communicating the longitudinal movement of the fetal head relative to the apparatus.

2. The apparatus of claim 1, wherein said movement indicator includes a sensor that contacts the fetal head.

3. The apparatus of claim 2, wherein said sensor defines a plunger disposed within a tube, said plunger moving axially in response to the longitudinal movement of the fetal head.

4. The apparatus of claim 3 wherein said plunger has an elastomeric distal tip for contacting the fetal head.

5. The apparatus of claim 4, wherein said movement indicator includes a fluid for communicating the axial movement of the plunger.

6. The apparatus of claim 5, wherein said movement indicator includes a manometer for indicating the axial movement of said plunger.

7. The apparatus of claim 6, which further includes a conduit disposed between the sensor and the manometer, said conduit providing a pathway for the fluid.

8. The apparatus of claim 7, wherein said fluid is air.

9. The apparatus of claim 1, which further includes a soft elastomeric liner positioned to cover at least a portion of said fetal head engaging portion of said pair of first members.

10. The apparatus of claim 9, wherein said opposite second end of each said first member defines a handle portion disposed for gripping by a user's hand.

11. An improved obstetrical forcep for assisting in the delivery of a baby, including a baby engaging portion and a handle portion disposed to be gripped by a user's hand wherein the improvement comprises a position detector attached to the forcep, said position detector sensing and communicating the longitudinal movement of the baby's head relative to the forcep.

12. The apparatus of claim 11, wherein said position detector includes a sensor for detecting the longitudinal movement of the head.

13. The apparatus of claim 12, wherein said sensor defines a plunger disposed within a tube, said plunger moving axially within said tube in response to the longitudinal movement of the baby's head.

14. The apparatus of claim 13, wherein said plunger has an elastomeric distal tip contactable with the fetal head.

15. The apparatus of claim 13, wherein said position detector includes a fluid for communicating the axial movement of the plunger.

16. The apparatus of claim 15, wherein said position detector includes a manometer, said manometer displaying the displacement of said plunger.

17. The apparatus of claim 16, which further includes a conduit disposed between the sensor and the manometer, said conduit providing a fluid pathway.

18. The apparatus of claim 11, which further includes a soft elastomeric liner, said liner covering at least a portion of said baby engaging portion of the forceps.

19. An apparatus for assisting in the delivery of a baby, comprising:

a delivery helmet disposable between a fetal head and a maternal birth canal for protecting the fetal head; and a position indicator mounted to said helmet, said position indicator sensing and communicating the longitudinal movement of the fetal head relative to said helmet.

20. The apparatus of claim 19, wherein said position indicator includes a sensor that contacts the fetal head.

21. The apparatus of claim 20, wherein said sensor defines a plunger disposed within a tube, said plunger moving within said tube in response to the longitudinal movement of the fetal head.

22. The apparatus of claim 21, wherein said plunger has an elastomeric distal tip for contacting the fetal head.

23. The apparatus of claim 21, wherein said position indicator includes a fluid for communicating the axial movement of the fetal head.

24. The apparatus of claim 23, wherein said position indicator includes a manometer, said manometer for indicating the movement of said plunger.

25. The apparatus of claim 24, which further includes a flexible tube connected between between the sensor and the manometer, said flexible tube providing a pathway for the fluid.

26. The apparatus of claim 19, which further includes an soft elastomeric lining, said lining covering at least a portion of said helmet disposed adjacent the fetal head.

27. The apparatus of claim 19 wherein said helmet includes a handle disposed for manipulating said helmet.

28. A method for assisting in the delivery of a baby, comprising:

inserting a delivery helmet into operative association between a fetal head and the mother;

positioning a movement detector against the crown of the fetal head for indicating and communicating the longitudinal movement of the fetal head relative to the delivery helmet; and pulling the delivery helmet longitudinally outward from the mother in response to the longitudinal movement of the fetal head relative to the delivery helmet.

29. The method of claim 28, which additionally includes filling the movement detector with fluid to obtain an initial reference value.

* * * * *